United States Patent [19]

Bogosian

[11] Patent Number: 5,834,243

[45] Date of Patent: Nov. 10, 1998

[54] DEFORMYLATION OF F-MET PEPTIDES IN BACTERIAL EXPRESSION SYSTEMS

[76] Inventor: Gregg Bogosian, 262 Village Mead Dr., Ballwin, Mo. 63021

[21] Appl. No.: 895,939

[22] Filed: Jul. 17, 1997

Related U.S. Application Data

[60] Provisional application No. 60/022,687, Jul. 19, 1996.

[51] Int. Cl.$^6$ ..................................................... C12P 21/02
[52] U.S. Cl. ...................... 435/69.1; 435/69.4; 435/228; 435/252.33; 435/320.1
[58] Field of Search .................................. 435/69.1, 69.4, 435/228, 252.33, 320.1

[56] References Cited

FOREIGN PATENT DOCUMENTS

WO 84 02351 A 6/1984 WIPO .............................. C12P 21/06

OTHER PUBLICATIONS

Guillon, Jean–Michel et al. (Jul. 1992) "Disruption of the Gene for Met–tRNAfMet Formyltransferase Severly Impairs Growth of *Escherichia coli*," Journal of Bacteriology, vol. 174, No. 13, pp. 4294–4301 (XP002043974).

Mazel, Didier et al. (1994) "Genetic characterization of polypeptide deformylase, a distinctive enzyme of eubacterial translation," *EMBO Journal*, vol. 13, No. 4, pp. 914–923 (XP002043973).

Warren, W.C. et al. (1996) "Increased production of peptide deformyulase eliminates retention of formylmethionine in bovine somatotropin overproduced in *Escherichia coli*," GENE, vol. 174, No. 2 pp. 235–238 (XP0043268).

Adams, J.M., (1968) "On the release of the formyl group from nascent protein," *J. Mol. Biol.* 33:571–589.

Azuma, C., et al., (1986) "Cloning of cDNA for human T–cell replacing factor (interleukin–5) and comparison with the murine homologue," *Nucleic Acids Res.* 14(22):9149–9158.

Bogosian, G., et al., (1989) "Biosynthesis and incorporation into protein of norllecuine by *Escherichia coli*," *J. Biol. Chem.* 264:531–539.

Bogosian, et al., (1990) Effect of protein overexpression on mistranslation in *Escherichia coli*. In; Hill, W.E., Dahlberg, A., Garrett, R.A., Moore, P.B., Schlessinger, D. and Warner, J.R. (Eds.), The Ribosome: Structure, Function and Evolution, American Society for Microbiology, Washington, D.C, pp. 546–558.

Calcott, Ph. H., et al., (1988) "Parameters affecting production of bovine somatotropin in *Escherichia coli* fermentations," *Dev. Indust. Microbiol.* 29:257–266.

Clogston, C.L., et al., (1992) "Detection and quantitation of recombinant granulocyte colony–stimulating factor charge isoforms: comparative analysis by cationic–exchange chromatography, isoelectric focusing gel electrophoresis, and peptide mapping," *Anal. Biochem.* 202:375–383.

Coleman, J., (1992) "Characterization of the *Escherichia coli* gene for 1–acyl–sn–glycerol–3–phosphate acyltransferase (plsC)," *Mol. Gen. Genet.* 232:295–303.

Derynck, R., et al., (1982) "Human interferon gamma is encoded by a single class of mRNA," *Nucleic Acids Res.* 10(12):3605–3615.

Doug, M.S. et al., (1995) "Retention of N–formylmethionine in recombinant bacterial cytochrome P450 enzymes containing the N–terminal sequence MALLLAVFL," *FASEB J.*, 9:A1486.

Eisenstein, E. (1991) "Cloning, Expression, Purification, and Characerterization of Biosynthetic Threonine Deaminase from *Escherichia coli*," *Journal of Biological Chemistry* 266(9):5801–5807.

Guillon, J.M., et al. (1992) "Disruption of the gene for Met–tRNA–fMET formyltranferase severely impairs growth of *Escherichia coli*," *J. Bacteriol.* 174:4294–4301/.

Gutterson, N.I., et al. (1983) "Replacement and amplication of bacterial genes with sequences altered in vitro," *Proc. Natl.Acad. Sci. USA* 80:4894–4898.

Hamilton, C.M., et al., (1989) "New Method for Generating Delections asnd Gene Replacements in *Escherichia coli*," *J. of Bacteriology* 171(9):4617–4622.

Hauschild–Rogat, P. (1968) "N–formylmethionine as a N–terminal group of *E. coli* ribosomal protein," *Mol. Gen. Genet.* 102:95–101.

Hirel, P.H., et al., (1989) "Extent of N–terminal methionine excision from *Escherichia coli* proteins is governed by the side–chain length of the penultimate amino acid," *Proc. Natl. Acad. Sci. USA* 86:8247–8251.

Hogset, A., et al., (1990) "Expression of Human Parathyroid Hormone in *Escherichia coli*," *Biochemical and Biophysical Research Communications* 166(1):50–60.

Honda, S., et al., (1989) "*Escherichia coli*–Derived Human Interfon–γ with Cys–Tyr–Cys at the N–Terminus is Partially $N^\alpha$–Acylated," *Archives of Biochemistry and Biophysics* 269:612–622.

Housman, D., et al., (1972) "Removal of formyl–methionine residue from nascent bacteriophage f2 protein," *J. Mol. Bio.* pp. 163–166.

Kane, J.F., et al., (1990) Commercial production of bovine somatotropin in *Escherichia coli*, In; Sikes, C.S. and Wheeler, A.P. (Eds.), Surface Reactive Peptides and Polymers: *Discovery and Commercialization*, American Chemical Society Books, Washington, D.C., pp. 186–200.

Livingston, D.M. and Leder, P., (1969) "Deformylation and protein synthesis," *Biochemistry* 20:435–443.

Marasco, W.A., et al., (1984) Purification and identification of formyl–methionyl–leucyl–phenylalanine as the major peptide neutrophil chemotatic produced by *Escherichia coli*, *J. Biol. Chem.* 259:5430–5439.

(List continued on next page.)

*Primary Examiner*—James Ketter
*Attorney, Agent, or Firm*—George R. Beck, Esq.; Arnold, White & Durkee

[57] ABSTRACT

A method for producing recombinant peptides and proteins having a diminished retention of N-formyl-methionine by coexpressing a peptide deformylase enzyme is disclosed. Also disclosed are substantially deformylated protein compositions and transformed bacterial cells and DNA vectors useful for acheiving such deformylation.

36 Claims, 2 Drawing Sheets

OTHER PUBLICATIONS

Mazel, D., et al., (1994) "Genetic characterization of polypeptide deformylase, a distinctive enzyme of eubacterial translation," *EMBO J.* 13:914–923.

Meinnel, T. and Blanquet, S., (1994) Characterization of the *Thermus thermophilus* locus encoding peptide deformylase and methionyl–tRNA–fMET formyltansferase, *J. Bacteriol.* 176:7387–7390.

Meinnel, T. and Blanquet, S., (1995) "Enzymatic properties of *Escherichia coli* peptide deformylase," *J. Bacteriol.* 177:1883–1887.

Meinnel, T. and Blanquet, S., (1993) "Evidence that peptide deformylase and methionyl–tRNA–fMET–formyltransferase are encoded within the same operon in *Escherichia coli*," *J. Bacteriol.* 175:7737–7740.

Meinnel, T., et al., (1993) Methionine as translation start signal: A review of the enzymes of the pathway in *Escherichia coli, Biochimie* (Paris) 75:1061–1075.

Milligan, D.L. and Koshland, Jr., D.E., (1990) "The amino terminus of the aspartate chemoreceptor is formylmethionine," *J. Biol. Chem.* 265:4455–4460.

Msokovitz, J., et al., (1995) "*Escherichia coli* Peptide Methionine Sulfoxide Reductase Gene: Regulation of Expression and Role in Protecting Against Oxidative Damage," *J. of Bacteriology* 177(3):502–507.

Nagata, S., et al., (1986) "Molecular cloning and expression of cDNA for human granulocyte colony–stimulating factor," *Nature* 319(6052):415–418.

Peredelchuk, M. Y. and Bennett, G.N., (1997) "A method for construction of *E. coli* strains with multiple DNA insertions in the chromosome," *Gene* 187:231–238.

Rabbani, S.A., et al., (1988) "Recombinant Human Parathyroid Hormone Synthesized in *Escherichia coli*," *J. of Biological Chemistry* 263(3):1307–1313/.

Rose, K., et al., (1992) "Human interleukin–5 expressed in *Escherichia coli* has N–terminal modifications," *Biochem. J.* 286:825–828.

Sandman, K., et al., (1995) "Improved N–terminal Processing of Recombinant Proteins Synthesized in *Escherichia coli*," *Biotechnology* 13:504–506.

Seeburg, P.H., et al., (1983) "Efficient bacterial expression of bovine and porcine growth hormones," *DNA* 2 pp. 37–45.

Specht, B., et al., (1994) "N–terminal variants of fatty acid–binding protein from bovine heart overexpressed in *Escherichia coli*," *J. Biotechnol.* 33:259–269.

Sugimoto, S., et al., (1990) "Isolation and characterization of recombinant eel growth hormone expressed in *Escherichia coli*," *J. Chromatog.* 515:483–494.

Sugino, T., et al., (1980) "Amino–terminally formylated tryptophan synthase α–subunit produced by the trp operon cloned in a plasmid vector," *J. Biochem.* 87:351–354.

Tsunasawa, S., et al., (1983) "Accumulation of amino–terminally formylated tryptophan synthase in amplifying conditions," *Agric. Biol. Chem.* 47(6):1393–1395.

Vianney A., et al., (1994) "Membrane Topology and mUtational Analysis of the TolQ protein of *Escherichia coli* Required for the Uptake of Macramolecules and Cell Envelope Integrity," *J. of Bacteriology* 176(3):822–829.

Wood, D.C., et al., (1989) "Purification and characterization of pituitary bovine somatotropin," *J. Biol. Chem.* 264:14741–14747.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:1:

```
GCATGAGTCG CATGCATTAA GTCTGGAGAT TTATGTCAGT T                    41
```

( 2 ) INFORMATION FOR SEQ ID NO:2:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:2:

```
TATGCGTCGG CAGAGACTTA AGCCCGGGCT TTCAGACG                        38
```

( 2 ) INFORMATION FOR SEQ ID NO:3:

( i ) SEQUENCE CHARACTERISTICS:
        ( A ) LENGTH: 507 base pairs
        ( B ) TYPE: nucleic acid
        ( C ) STRANDEDNESS: single
        ( D ) TOPOLOGY: linear     ( i x ) FEATURE:
        ( A ) NAME/KEY: CDS
        ( B ) LOCATION: 1..507

( x i ) SEQUENCE DESCRIPTION: SEQ ID NO:3:

```
ATG TCA GTT TTG CAA GTG TTA CAT ATT CCG GAC GAG CGG CTT CGC AAA    48
Met Ser Val Leu Gln Val Leu His Ile Pro Asp Glu Arg Leu Arg Lys
 1               5                  10                  15

GTT GCT AAA CCG GTA GAA GAA GTG AAT GCA GAA ATT CAG CGT ATC GTC    96
Val Ala Lys Pro Val Glu Glu Val Asn Ala Glu Ile Gln Arg Ile Val
                20                  25                  30

GAT GAT ATG TTC GAG ACG ATG TAC GCA GAA GAA GGT ATT GGC CTG GCG   144
Asp Asp Met Phe Glu Thr Met Tyr Ala Glu Glu Gly Ile Gly Leu Ala
             35                  40                  45

GCA ACC CAG GTT GAT ATC CAT CAA CGT ATC ATT GTT ATT GAT GTT TCG   192
Ala Thr Gln Val Asp Ile His Gln Arg Ile Ile Val Ile Asp Val Ser
         50                  55                  60

GAA AAC CGT GAC GAA CGG CTA GTG TTA ATC AAT CCA GAG CTT TTA GAA   240
```

```
Glu  Asn  Arg  Asp  Glu  Arg  Leu  Val  Leu  Ile  Asn  Pro  Glu  Leu  Leu  Glu
 65                      70                      75                      80

AAA  AGC  GGC  GAA  ACA  GGC  ATT  GAA  GAA  GGT  TGC  CTG  TCG  ATC  CCT  GAA    288
Lys  Ser  Gly  Glu  Thr  Gly  Ile  Glu  Glu  Gly  Cys  Leu  Ser  Ile  Pro  Glu
                    85                      90                           95

CAA  CGT  GCT  TTA  GTG  CCG  CGC  GCA  GAG  AAA  GTT  AAA  ATT  CGC  GCC  CTT    336
Gln  Arg  Ala  Leu  Val  Pro  Arg  Ala  Glu  Lys  Val  Lys  Ile  Arg  Ala  Leu
               100                      105                     110

GAC  CGC  GAC  GGT  AAA  CCA  TTT  GAA  CTG  GAA  GCA  GAC  GGT  CTG  TTA  GCC    384
Asp  Arg  Asp  Gly  Lys  Pro  Phe  Glu  Leu  Glu  Ala  Asp  Gly  Leu  Leu  Ala
               115                      120                     125

ATC  TGT  ATT  CAG  CAT  GAG  ATG  GAT  CAC  CTG  GTC  GGC  AAA  CTG  TTT  ATG    432
Ile  Cys  Ile  Gln  His  Glu  Met  Asp  His  Leu  Val  Gly  Lys  Leu  Phe  Met
          130                      135                     140

GAT  TAT  CTG  TCA  CCG  CTG  AAA  CAA  CAA  CGT  ATT  CGT  CAG  AAA  GTT  GAA    480
Asp  Tyr  Leu  Ser  Pro  Leu  Lys  Gln  Gln  Arg  Ile  Arg  Gln  Lys  Val  Glu
145                      150                     155                     160

AAA  CTG  GAT  CGT  CTG  AAA  GCC  CGG  GCT                                         507
Lys  Leu  Asp  Arg  Leu  Lys  Ala  Arg  Ala
                    165
```

( 2 ) INFORMATION FOR SEQ ID NO:4:

( i ) SEQUENCE CHARACTERISTICS:
      ( A ) LENGTH: 169 amino acids
      ( B ) TYPE: amino acid
      ( D ) TOPOLOGY: linear ( i i ) MOLECULE TYPE: protein ( x i ) SEQUENCE DESCRIPTION: SEQ ID NO:4:

```
Met  Ser  Val  Leu  Gln  Val  Leu  His  Ile  Pro  Asp  Glu  Arg  Leu  Arg  Lys
 1              5                      10                      15

Val  Ala  Lys  Pro  Val  Glu  Glu  Val  Asn  Ala  Glu  Ile  Gln  Arg  Ile  Val
               20                      25                      30

Asp  Asp  Met  Phe  Glu  Thr  Met  Tyr  Ala  Glu  Glu  Gly  Ile  Gly  Leu  Ala
               35                      40                      45

Ala  Thr  Gln  Val  Asp  Ile  His  Gln  Arg  Ile  Ile  Val  Ile  Asp  Val  Ser
          50                      55                      60

Glu  Asn  Arg  Asp  Glu  Arg  Leu  Val  Leu  Ile  Asn  Pro  Glu  Leu  Leu  Glu
 65                      70                      75                      80

Lys  Ser  Gly  Glu  Thr  Gly  Ile  Glu  Glu  Gly  Cys  Leu  Ser  Ile  Pro  Glu
                    85                      90                      95

Gln  Arg  Ala  Leu  Val  Pro  Arg  Ala  Glu  Lys  Val  Lys  Ile  Arg  Ala  Leu
               100                     105                     110

Asp  Arg  Asp  Gly  Lys  Pro  Phe  Glu  Leu  Glu  Ala  Asp  Gly  Leu  Leu  Ala
               115                     120                     125

Ile  Cys  Ile  Gln  His  Glu  Met  Asp  His  Leu  Val  Gly  Lys  Leu  Phe  Met
          130                     135                     140

Asp  Tyr  Leu  Ser  Pro  Leu  Lys  Gln  Gln  Arg  Ile  Arg  Gln  Lys  Val  Glu
145                     150                     155                     160

Lys  Leu  Asp  Arg  Leu  Lys  Ala  Arg  Ala
                    165
```

DEFORMYLATION OF F-MET PEPTIDES IN BACTERIAL EXPRESSION SYSTEMS

This application claims the benefit of provisional application Ser. No. 60/022,687, filed Jul. 19, 1996.

FIELD OF THE INVENTION

The present invention is directed to materials and methods useful in production of recombinant proteins in transformed bacteria. In one important embodiment, the present invention is directed to materials and methods useful in diminishing the retention of N-formyl groups on the N-terminal methionine residues of recombinant proteins produced at high levels in transformed bacterial host cells. In another embodiment, novel methods for increasing the levels of peptide deformylase in transformed bacterial host cells are disclosed.

BACKGROUND OF THE INVENTION

Methionine is the universal starting amino acid residue for growing peptide chains (e.g., protein synthesis) in most living systems. In order for methionine to function as the initiating amino acid for nascent peptide synthesis in bacteria, it must undergo a series of transformations both before initiation of protein synthesis and after the protein has been made (see review by Meinnel, T., Mechulam, Y., and Blanquet, S., 1993). In *E. coli*, all of the enzymes involved in these transformations and their respective genes have been isolated and/or sequenced (Meinnel, T. and Blanquet, S., 1994).

Two of the most notable transformations in the initiating amino acid methionine amino acid involve the addition of an N-formyl group to methionine molecules prior to the initiation of messenger RNA (mRNA) translation and the subsequent removal of the N-formyl group from the amino (N-) terminal methionine of the nascent peptide. The removal of the N-formyl group is accomplished by the enzyme peptide deformylase (EC 3.5.1.27 according to the IUB nomenclature as published in "Enzyme Nomenclature Recommendations" (1992) Academic Press, San Diego). Peptide deformylase (PDF) cleaves the formyl group from most nascent formyl-methionine-peptides in a substrate specific reaction. However, there are exceptions to the routine action of PDF. For example, some *E. coli* proteins remain either wholly or partially formylated. (Hauschild-Rogat, P., 1968; Marasco, W. A., et al., 1984; and Milligan, D. L. and Koshland, Jr., D. E., 1990). It has also been observed that several recombinant proteins which are normally free of N-formyl-methionine (f-Met) exhibit a significant retention of f-Met when they are overproduced in recombinant *E. coli* strains. Examples of this phenomenon include *E. coli* tryptophan synthase alpha- and beta-subunits (Sugino, Y., et al., 1980; Tsunasawa, S., et al., 1983); bovine somatotropin (BST) (Bogosian, G., et al., 1989); eel growth hormone (Sugimoto, Y., et al., 1990); *E. coli* 1-acyl-sn-glycerol-3-phosphate acyltransferase (Coleman, J., 1992); human granulocyte colony-stimulating factor (Clogston, C. L., et al., 1992); bovine fatty acid-binding protein (Specht, B., et al., 1994); bovine cytochrome P450 (Dong, M. S., et al. 1995); methanothermus fervidus histone A (Sandman, K., et al., 1995); human interleukin-5 (Rose, K., et al., 1992); human parathyroid hormone (Rabbani, S., et al., 1988; Hogset, A., et al., 1990); human gamma-interferon (Honda, S., et al., 1989); *E. coli* threonine deaminase (Eisenstein, 1991); and *E. coli* TolQ membrane protein (Vianney, A., et al., 1994).

Retention of the formyl group on a protein expressed in and purified from bacterial expression systems is undesireable when preparing recombinant pharmaceuticals. As a result, complex and expensive purification procedures are required to purify the deformylated protein of interest to a degree sufficient to qualify it for pharmaceutical use. In addition, costly analytical methods to quantify the formylated isoform must frequently be devised in order to insure that the level of such isoform in the final product is below a desired level. Therefore, there exists a need to achieve the efficient removal of undesirably retained N-formyl groups on recombinant proteins without interfering with the level of recombinant protein production in bacterial expression systems.

SUMMARY OF THE INVENTION

The present invention relates to the discovery of methods and materials useful in removing retained N-formyl groups from nascent recombinant N-formyl methionine peptides produced in transformed bacterial hosts (e.g., *E. coli*). In a general and overall sense, the invention provides methods which are capable of reducing the occurrence of retained N-formyl groups on recombinant, bacterially-expressed recombinant peptides or proteins (collectively referred to as "recombinant proteins"), without substantially decreasing the level of recombinant protein production, by causing the bacterial host cells to increase expression and/or activity of PDF, for example by genetic or epigenetic manipulations. Preferably, this result is achieved by transforming an expressible PDF gene into suitable bacterial host cells so that the level of PDF is increased in the bacterial host cells. Also included within the invention are the host cells so transformed and the substantially deformylated recombinant protein so produced.

In one preferred embodiment, the present invention provides a method for production, in transformed bacterial host cells, of recombinant protein having a diminished retention of N-formyl methionine. This method includes the step of transforming bacterial host cells with DNA comprising a first expressible DNA sequence encoding a peptide deformylase enzyme also operably linked to a promoter operable in the bacterial host cells and a second expressible DNA sequence encoding a recombinant protein also operably linked to a promoter operable in the bacterial host cells. The expressible DNA sequences may be present on a single DNA segment or, alternatively, on different segments which may be co-transformed into the bacterial host cells. One may then identify transformed bacterial host cells having both the first and second expressible sequences and culture the transformed bacterial host cells under conditions which cause coexpression of the recombinant protein and the PDF enzyme, resulting in substantial deformylation of the coexpressed recombinant protein.

In a more preferred embodiment, each expressible DNA sequence is on a DNA molecule containing a marker gene so that transformed bacterial host cells may be identified by selecting bacteria having a marker trait conferred by the marker gene.

In another preferred embodiment, the recombinant protein produced in the transformed host cell has both a diminished retention of N-formyl methionine and a level of recombinant protein production which is substantially equivalent (i.e., at least about 80%) of that of otherwise identical host cells transformed only with a DNA molecule comprising the gene encoding the recombinant protein.

In yet another embodiment, the present invention provides a novel method for increasing the level of PDF in transformed bacterial host cells which includes transforming the host cells with an expressible DNA sequence encoding a peptide deformylase enzyme operably linked to a promoter operable in the host cells. In a preferred embodiment, the DNA used for transformation will also contain a marker gene. The transformed host cells may then be identified by virtue of having a marker trait conferred by the marker gene. The transformed host may be used as a universal expression system for expression of proteins for which retention of N-formyl methionine is desired to be decreased.

Additional embodiments relate to cells coexpressing genes encoding PDF and the recombinant protein of interest and to vectors encoding PDF and the recombinant protein of interest.

DESCRIPTION OF THE FIGURES

FIGS. 2 and 2A. RP-HPLC analyses of BST isolated from induced cultures of W3110G[pBGH1] (A) and W3110G [pXT179] (B). Absorbance has been converted to millivolts for determination of area under the peaks. The two observable components are: 1. normal BST; and 2. BST containing a formyl group on the N-terminal methionine. The latter species was identified by both mass spectrometry and by hydrolysis to remove the formyl group from the protein, followed by RP-HPLC. The strains W3110G[pBGH1] and W3110G[pXT179] were grown in 10 liter fermentation vessels and induced with indole acrylic acid (Bogosian, G., et al., 1989). Inclusion bodies containing BST were isolated from the cultures by homogenization and centrifugation, and the BST was dissolved and refolded (Bogosian, G., et al., 1989). The BST was further purified by DEAE-cellulose ion-exchange chromatography (Wood, D. C., et al., 1989). From this material, formylated BST was separated from the total BST with a Perkin-Elmer Series 4 RP-HPLC system using a Vydac C-18 column. The chromatographic conditions were a flow rate of 1.5 ml/min with constant 40 mM trifluoroacetic acid, and 54–60% acetonitrile over 24 min followed by 60–75% acetonitrile over 6 min. The lower limit for detection of the formylated BST is approximately 0.5% of the total BST.

DESCRIPTION OF ILLUSTRATIVE EMBODIMENTS

One of the major drawbacks of expressing pharmaceutically useful recombinant proteins in procaryotic expression systems is the undesirable retention of formylated isoforms, resulting in large scale production systems being more expensive and less efficient than they should be. Therefore, a goal of the present invention is to achieve the efficient removal of retained N-formyl groups on recombinant proteins without significantly decreasing with the level of production of such proteins in procaryotic expression systems.

In one embodiment, the bacterial host cells expressing a recombinant protein of interest are transformed with a gene encoding a PDF enzyme so that the PDF expression level is increased in the cell relative to the level of its original expression. For the purpose of the present invention, the retention of N-formyl methionine is diminished if the recombinant protein product of interest is less formylated than it would have been if produced in a bacterial host cell which, otherwise identical, has not been transformed with a gene encoding the PDF enzyme.

The genetic material encoding the PDF enzyme may be prepared using any number of techniques known to those of skill in the art including, but not limited to, PCR technology, cloning from DNA genomic libraries, or cDNA cloning from messenger RNA, using any of a number of applicable screening processes known to those of skill in the art to identify clones having the PDF gene. PCR technology is described in Ronald M. Atlas and S. Asimk Bej, Polymerase Chain Reaction, pp. 418–435 in *Methods for General and Molecular Biology*, Philipp Gerhardt American Society of Microbiology, Wash. D.C. 1994 and other cloning techniques are described in Sambrook, et al. Molecular Cloning Manual, 2d Edition, 1989, each of which are incorporated herein by reference.

One embodiment of the present invention is a method for increasing the amount of PDF produced in transformed bacterial host cells which comprises (i) transforming the host cells with a DNA vector comprising a marker gene and a DNA sequence encoding a PDF enzyme operably linked to a promoter operable in the host cells, (ii) identifying transformed host cells having a marker trait conferred by the marker gene, and (iii) culturing the transformed host cells under conditions which cause them to produce more PDF than untransformed bacteria. This method produces a universal host which can be further transformed with a gene encoding a recombinant protein of interest for which one desires to decrease retention of N-formyl methionine. A variety of inducible control systems can be employed to vary the level of PDF and any one is suitable for use in this invention. In a preferred embodiment, the promoter to which the PDF is linked is chemically inducible and the transformed *E. coli* is cultured in the presence of an amount of inducer compound sufficient to increase PDF production to a desired level. In the most preferred embodiment, the promoter is an indole acrylic acid inducible trp promoter and the inducer compound is indole acrylic acid. The desired level of PDF, which will vary depending on the control system employed, is between the production level of untransformed *E. coli* and the maximal production level of the transformed *E. coli*. One skilled in the art can determine what particular level of PDF is desired and which control system should be employed to meet the artisan's specific requirements. A number of promoters known to those of skill in the art can be employed in the instant invention including lac, tac, rec A, ara, and lambda pl.

The present invention is also directed toward the transformed bacterial host cells which produce increased levels of PDF. The bacterial strain employed may be of any species which can be transformed. Preferably, the bacteria is a member of the enterobacteriaceae family. In a preferred embodiment, the bacteria is *E. coli*, most preferably an *E. coli* K12 strain.

In another embodiment, the present invention provides a method for deformylating recombinant protein produced in bacteria, which comprises increasing production of a PDF enzyme in the bacteria in which the recombinant protein is also produced. With this method one may culture the transformed bacteria under conditions which cause coexpression of the recombinant protein and the PDF enzyme. The PDF gene and the gene encoding the recombinant protein of interest are each configured so that they are operably linked to a suitable promoter of interest capable of directing expression of the PDF and the recombinant protein of interest. In one preferred embodiment, the DNA sequences encoding the recombinant protein and PDF enzyme are on the same DNA molecule and are operably linked to the same promoter. Preferably, these two sequences are under the regulation of the indole acrylic acid inducible trp promoter with no transcription terminator between the two genes, although other promoters and configurations could be determined and used by those of skill in the art. In another embodiment, the two sequences are on the same molecule but are operably linked to separate promoters, which may be of the same or of different types.

In yet another embodiment, the two sequences are present on two different DNA molecules and are under the control of separate promoters, which also may be of the same or different types. Thus, although the trp promoter is used in the preferred embodiment to drive expression of both the PDF gene and the gene encoding the desired polypeptide of interest, it is not necessary that the trp promoter be used or even that both genes be driven by the same promoter. Alternative embodiments allow selection of a promoter to achieve the desired level of expression in a given cell type.

It is important to select a PDF gene which is compatible with the bacterial host so that it will be functionally expressed in the bacterial host. Preferably, therefore, the DNA sequence encoding the PDF is substantially the same as the DNA sequence encoding the PDF enzyme endogenous to the bacterial strain employed. In a preferred embodiment, the strain and the PDF enzyme are from $E.$ $coli$, and in an even more preferred embodiment the gene is from an $E.$ $coli$ K12 strain and introduced to a strain of that same genotype. For the purposes of this invention, an $E.$ $coli$ PDF gene is one which encodes a PDF enzyme whose amino acid sequence is substantially similar to the amino acid sequence of the $E.$ $coli$ PDF enzyme and which is expressible and operable in the $E.$ $coli$ host.

The "gene" encoding the protein of interest may be selected from any of a number of heterologous genes or cDNAs designed for protein production in the procaryotic host. Since procaryotic transcriptional/translational machinery is unable to recognize and remove the introns frequently present in unprocessed eucaryotic RNA, if the gene of interest in the present invention is a eucaryotic gene which contains introns, the corresponding cDNA, rather than the gene itself, is used as the source of DNA introduced into the bacterial strain being used to produce the recombinant protein. In the most preferred embodiment, the gene of interest encodes somatotropin. In another preferred embodiment, the gene of interest encodes human granulocyte colony stimulating factor. However, other genes encoding recombinant proteins which retain an unacceptable proportion of formylated N-terminal methionine isoforms are suitable as well, including human interleukin 5 (IL-5), human parathyroid hormone, eel growth hormone, 1-acyl-sn-glycerol-3-phosphate acyltransferase, bovine fatty acid binding protein, bovine cytochrome p450 and human gamma-interferon.

Optimally, the system should be constructed so as to allow for a level of enhanced PDF expression that does not occur at the expense of the level of expression of the protein of interest. In a most preferred embodiment, the present invention provides a method for significantly diminishing the retention of N-formyl methionine without substantially decreasing the amount of recombinant protein produced. Accordingly, the transformed bacteria most preferably produce the recombinant protein at a level which is greater than about 80% of the level produced by bacteria which, otherwise identical, do not contain the DNA sequence encoding a PDF enzyme.

Prior to transformation into the bacterial host, the DNA segments encoding the PDF and gene encoding the protein of interest may be incorporated in any of a number of suitable vectors for transformation into the bacterial host.

Suitable vectors include plasmid vectors, cosmid vectors, and phage vectors variously known to those of skill in the art, for example, as described by Sambrook, et al. The PDF gene and the gene encoding the protein of interest may be on the same or separate molecules, preferably with each DNA molecule containing a marker gene so that transformed bacterial host cells can be identified. When the genes are provided on separate molecules, the bacterial host can be transformed with both of the DNA molecules simultaneously or at different times. For example, in one embodiment, the bacteria are transformed with a vector which contains the gene encoding the PDF, which may then be stably integrated into the chromosome. The resulting transformed bacteria can then be maintained and transformed at will with the second vector encoding a protein of interest. The method of transformation is not critical although it may be preferred that the cells be transformed using a vector that undergoes stable chromosomal integration. One vector of this type is bacteriophage lambda. Another example is the bacteriophage Mu vector disclosed in U.S. Pat. No. 5,395,763. This Mu vector would be particularly advantageous if used in the present invention because of its greater stability relative to plasmid vectors, its smaller size relative to bacteriophage lambda and its potential for tight regulation of recombinant protein gene expression. Another approach for constructing $E.$ $coli$ strains with multiple, stable chromosomal insertions has been described which is based on elements of modules for site specific recombination of Tn1545 and phage lambda (Peredelchuk, M. and Bennet, G., 1997).

One skilled in the art would recognize and appreciate that numerous alternative embodiments of this invention could involve approaches to manipulate endogenous PDF expression and/or activity. For example, a variety of stategies for the targeted replacement or modification of endogenous bacterial chromosomal regions have been described (see for example, Gutterson, N. I. and Koshland, D., 1983; Hamilton, C., et al., 1989; Moskovitz, J., et al., 1995). One could use such an an approach to introduce genetic modifications in $E.$ $coli$ that would result in increased PDF expression/activity. For example, the endogenous PDF promoter could be replaced with a strong promoter, such as the trp promoter, which would drive higher levels of PDF expression. In addition, the endogenous PDF promoter could be modified in a way that would either remove a negative transcriptional regulatory element or introduce a regulatory element which could enhance transcription. As an additional means by which PDF expression could be enhanced, a recombinant DNA molecule could be introduced into the bacterial cells which would cause the production of a protein capable of enhancing endogenous PDF activity, such as a transcription factor, a protein which physically interacts with PDF as a positive regulator, or a protein which functions as a positive upstream regulator of PDF. Alternatively, one could remove or eliminate a protein which normally serves in some fashion as a negative regulator of PDF expression and/or activity. This could be accomplished, for example, by using a genetic modification stategy as mentioned above to eliminate or impair the gene encoding the negative regulator, or by using antisense inhibition of gene expression to inhibit the production of the negative regulator.

According to the present invention one may produce a composition comprising a recombinant protein produced from bacteria which is 96 to 100% deformylated. More preferably, the composition is 98 to 100% deformylated. The most preferred composition comprises bovine somatotropin.

Another preferred composition comprises human granulocyte colony stimulating factor.

The following examples are intended to illustrate a preferred embodiment of the present invention but not to limit it.

Preparation of expression systems in which the retention of various N-formylated proteins has been reduced by transformation of bacterial hosts with a DNA vectors encoding peptide deformylase and the recombinant protein of interest are presented.

EXAMPLE 1

Cloning of the *E. coli* PDF Gene

In this example, introduction of the PDF and bovine somatotropin genes under the control of a trp promoter resulted in a reduction of N-formylated BST from a level of about five percent of total BST in a control strain which contained the BST gene but not the PDF gene on the plasmid, to an undetectable level for strains containing both genes.

Primers flanking both ends of the *E. coli* PDF gene were based on the published nucleotide (nt) sequence for this region (Guillon, J. M., et al., 1992). The forward (initiation end of the gene) primer had the sequence 5'-GCATGAGTCGCATGCATTAAGTCTGGAGATT TATGTCAGTT-3' (SEQ. ID NO:1), which includes a recognition site for the restriction endonuclease SphI (GCATGC). The reverse (termination end of the gene) primer had the sequence 5'-GCAGAGTATGCG TCGACTTAAGCCCGGGCTTTCAGACG-3' (SEQ. ID NO:2), which includes a recognition site for the restriction endonuclease SalI (GTCGAC). In a PCR reaction, these primers delimit an amplified product which includes the entire PDF structural gene including the native ribosomal binding site, but without any associated promoters or other regulatory sequences (Guillon, J. M., et al., 1992). The PCR was performed usingas a template chromosomal DNA from *E. coli* K-12 strain W3110G (Bogosian, G., et al., 1989), resulting in the predicted 500 base-pair product which was then cloned and nt sequenced. The PDF nucleotide sequence thus obtained was identical in all respects to that published previously (Guillon, J. M., et al., 1992; Mazel, D., et al., 1994).

EXAMPLE 2

Construction and Properties of pXT179

Figure 1:
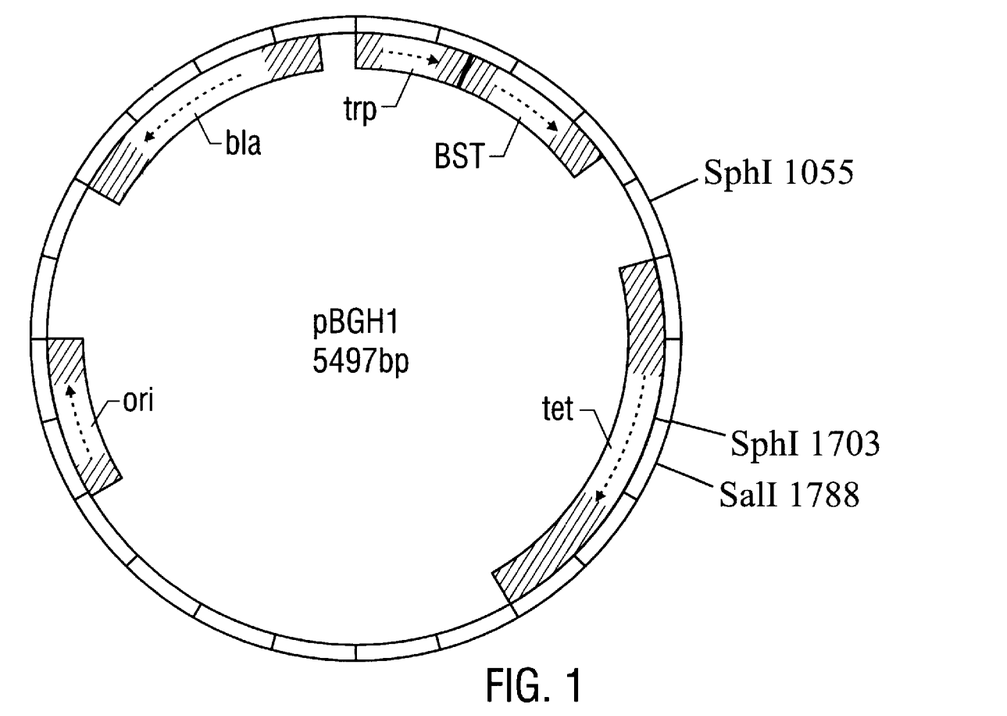
FIG. 1. Plasmids pBGH1 and pXT179.
Figure 1A:
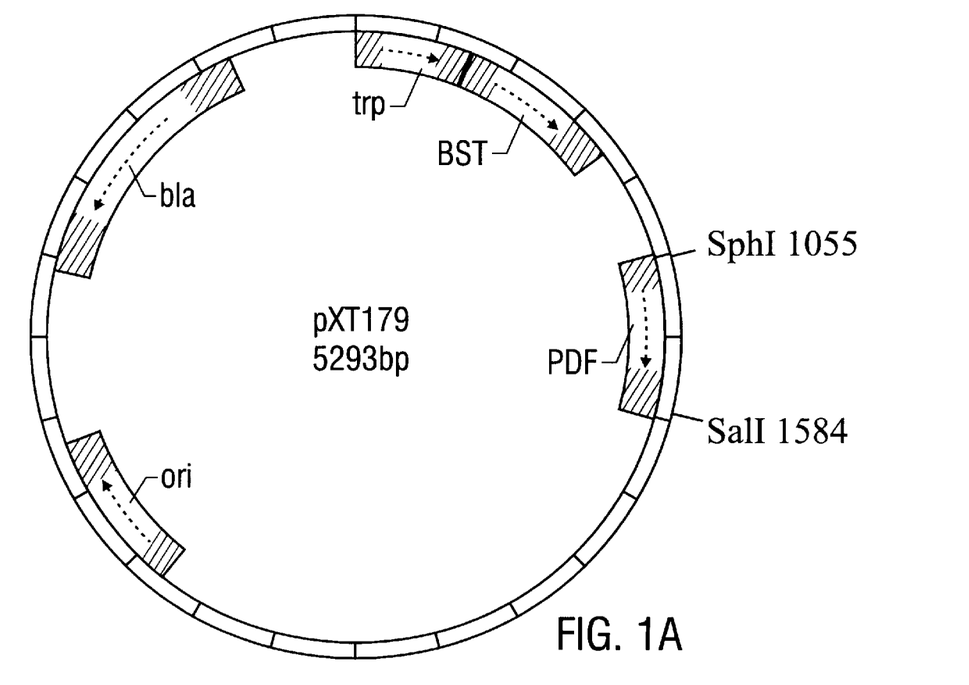

The 500 bp PCR product containing the PDF gene was digested with SphI and SalI and subcloned into the SphI and SalI sites on pBGH1, a plasmid vector which can be used for overproduction of bovine somatotropin (BST) and which has been described previously (Seeburg, P. H., et al., 1983; Calcott, P. H., et al., 1988; Bogosian, G., et al., 1989, 1990; Kane, J. F., et al., 1990). The resulting construct was designated pXT179, a plasmid in which the BST and PDF genes are under the regulation of the trp promoter. There is no transcription terminator between the BST and PDF genes in the vector. High-level synthesis of proteins encoded by genes under the control of the trp promoter on such plasmids can be achieved by culturing a strain transformed with pXT179 without tryptophan in the presence of the inducer indole acrylic acid (IAA) (Calcott, P. H., et al., 1988; Bogosian, G., et al., 1989; Kane, J. F., et al., 1990). To determine the effect of the PDF gene on the level of retained formylated BST, *E. coli* K-12 strain W3110G was transformed with both pBGH1 and pXT179, resulting in two strains designated W3110G[pBGH1] and W3110G [pXT179], respectively. Both strains produced BST at about 30% of total cell protein.

EXAMPLE 3

PDF Production and the Deformylation of BST

Figure 2:
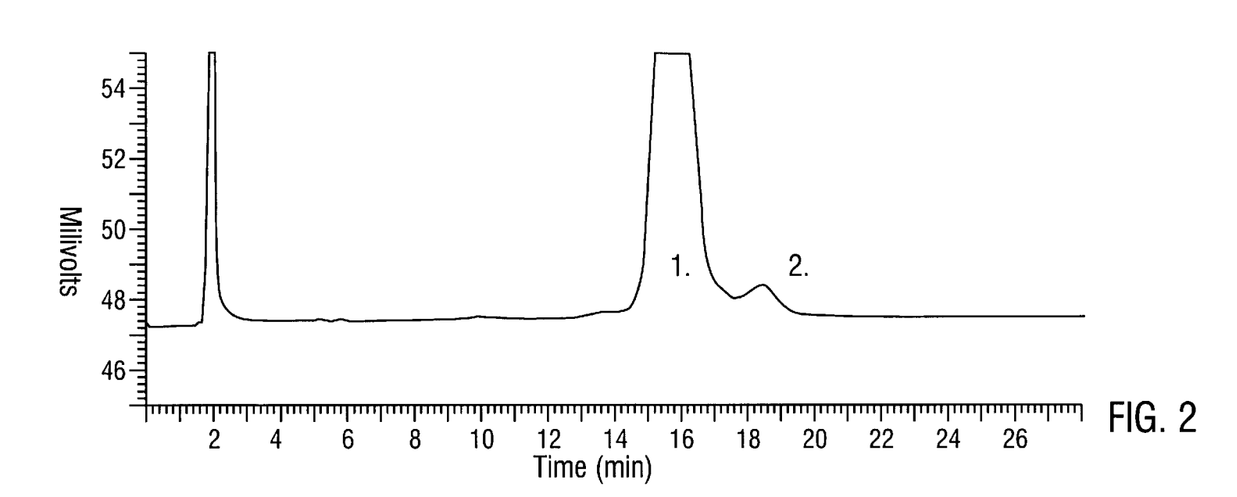
Figure 2A:
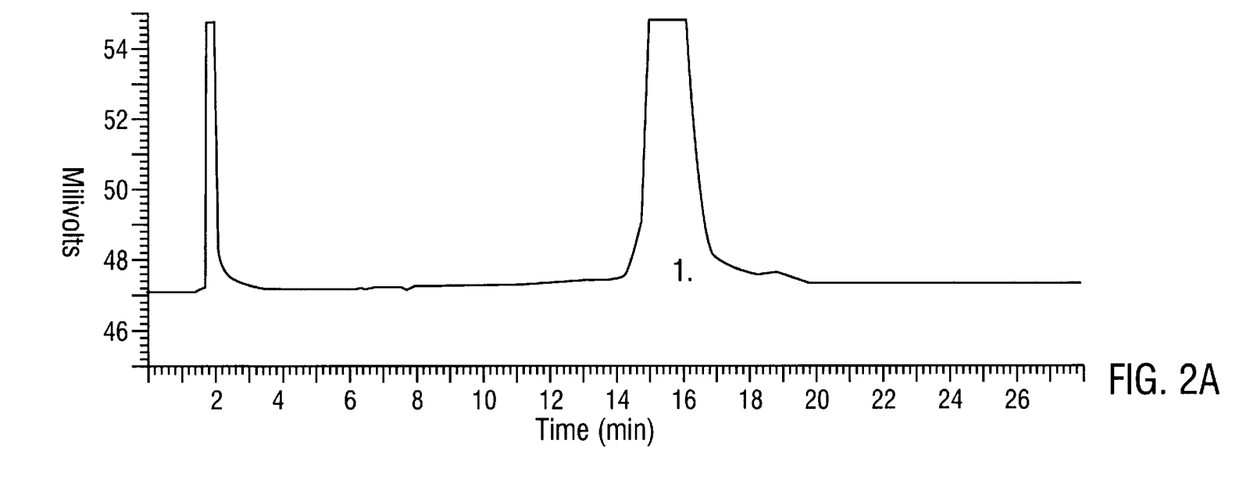

Crude extracts prepared from IAA-induced cultures of the two transformed strains were assayed for PDF activity by the method of Adams (1968). Each assay was performed in triplicate on three independent cultures of each strain. The crude cellular extract from strain W3110G[pXT179] had over 40 times as much PDF activity as the extract from strain W3110G[pBGH1] (110±10 versus 2.6±0.8 units, respectively). BST was isolated from both strains and subjected to RP-HPLC analyses to estimate the f-Met retention. Each of these analyses was performed in duplicate on each sample. BST purified from the strain W3110G[pBGH1] exhibits two peaks under such conditions. A representative RP-HPLC profile is shown in FIG. 2. The larger peak is Met-BST, and the smaller peak is f-Met-BST (Bogosian, G., et al., 1989), representing about 5% of the total BST produced. The minor second peak in the RP-HPLC profile for the BST purified from the strain W3110G[pXT179] appeared not to contain f-Met-BST since the f-Met-BST peak had a retention time of about 18.4 minutes and the minor second peak had a retention time of about 18.8 minutes. However, to rule out this possibility, the material comprising the minor peak was isolated and subjected to electrospray mass spectrometry, which confirmed the absence of f-Met-BST. The BST from this minor peak had a mass 42–46 daltons greater than Met-BST but addition of a formyl group to Met-BST would increase the mass by only 28 daltons. The minor peak material is most likely BST carbamylated at a lysine residue, which would increase the mass by 43 daltons. The use of urea for dissolution of BST inclusion bodies in the purification method employed here (Bogosian, G., et al., 1989) is known to result in carbamylation of lysine in a very small fraction of the BST (unpublished observations). Thus, while the f-Met-BST isoform was present at a level of about 5% of the total BST produced in the W3110G[pBGH1] strain, it was reduced to undetectable levels in the strain with elevated levels of PDF (i.e., W3110G[pXT179]).

The above data yield three significant observations. First, the PDF gene obtained from *E. coli* K-12 strain W3110G and used in the above examples is identical to the PDF gene from other *E. coli* strains. Second, an *E. coli* strain expressing the PDF gene under the control of the trp promoter on a high-copy number plasmid had levels of PDF over 40-fold higher than the corresponding strain with a single chromosomal copy of the PDF gene. Third, high-level coexpression of the BST and PDF genes resulted in the elimination of detectable f-Met-BST. This approach should be generally applicable for the prevention of f-Met retention in proteins expressed in *E. coli* or other organisms. These data demonstrate the utility of overexpressing PDF as a means of removing retained formyl groups from bacterially expressed recombinant proteins.

EXAMPLE 4

Production of Deformylated Human Granulocyte Colony-Stimulating Factor (GCSF)

PCR primers are designed based upon published GCSF cDNA sequence (Tsuchiya, N., et al., 1986) which delimit an amplified product which includes the entire GCSF stuctural coding region including the native ribosomal binding site. PCR is performed using as a template plasmid containing the GCSF cDNA, and the resulting product is sequenced in order to verify that it is identical with the corresponding published sequence.

Using standard molecular biological techniques (for example as described in Sambrook, 1989) the PCR product is digested with appropriate restriction enzyme(s) and subcloned into pBGH1 in place of the sequences encoding BST. The resulting plasmid will therefore contain the GCSF gene under the control of the trp promoter. The 500 bp PCR product containing PDF (as described in Example 1) is restriction digested and subcloned into the trp-GCSF plasmid so that a new plasmid is generated in which both PDF and GCSF are under the control of the trp promoter.

To determine the effect of the PDF gene on the level of retained formylated GCSF, *E. Coli* K-12 strain W3110G is transformed to produce two transformant strains, one with the plasmid containing PDF and GCSF and one with the plasmid containing only GCSF. High level synthesis of the proteins is achieved by culturing W3110G in the presence of IAA as described. Crude extracts prepared from IAA-induced cultures of the two transformed strains are assayed for PDF activity by the method of Adams (1968) and recombinant GCSF is isolated from both strains and analyzed by RP-HPLC to evaluate f-Met retention. Using this approach, results would be obtained similar to those described for BST in Example 3. Thus, levels of detectable f-Met- GCSF would be advantageously eliminated.

EXAMPLE 5

Production of Deformylated Human Interleukin-5 (IL-5)

PCR primers are designed based upon published IL-5 cDNA sequence (Azuma, C., et al., 1986) which delimit an amplified product which includes the entire IL-5 stuctural coding region including the native ribosomal binding site. PCR is performed using as a template plasmid containing the IL-5 cDNA, and the resulting product is sequenced in order to verify that it is identical with the corresponding published sequence.

Using standard molecular biological techniques (for example as described in Sambrook, 1989) the PCR product is digested with appropriate restriction enzyme(s) and subcloned into pBGH1 in place of the sequences encoding BST. The resulting plasmid will therefore contain the IL-5 gene under the control of the trp promoter. The 500 bp PCR product containing PDF (as described in Example 1) is restriction digested and subcloned into the trp-IL-5 plasmid so that a new plasmid is generated in which both PDF and IL-5 are under the control of the trp promoter.

To determine the effect of the PDF gene on the level of retained formylated IL-5, *E. Coli* K-12 strain W3110G is transformed to produce two transformant strains, one with the plasmid containing PDF and IL-5 and one with the plasmid containing only IL-5. High level synthesis of the proteins is achieved by culturing W3110G in the presence of IAA as described. Crude extracts prepared from IAA-induced cultures of the two transformed strains are assayed for PDF activity by the method of Adams (1968) and recombinant IL-5 is isolated from both strains and analyzed by RP-HPLC to evaluate f-Met retention. Using this approach, results would be obtained similar to those described for BST in Example 3. Thus, levels of detectable f-Met- IL-5 would be advantageously eliminated.

EXAMPLE 6

Production of Deformylated Human Gamma-Interferon (IFN-Gamma)

PCR primers are designed based upon published IFN-gamma cDNA sequence (Leung, D., et al., 1982) which delimit an amplified product which includes the entire IFN-gamma stuctural gene including the native ribosomal binding site. PCR is performed using as a template plasmid containing the IFN-gamma cDNA, and the resulting product is sequenced in order to verify that it is identical with the corresponding published sequence.

Using standard molecular biological techniques (for example as described in Sambrook, 1989) the PCR product is digested with appropriate restriction enzyme(s) and subcloned into pBGH1 in place of the sequences encoding BST. The resulting plasmid will therefore contain the IFN-gamma gene under the control of the trp promoter. The 500 bp PCR product containing PDF (described in Example 1) is restriction digested and subcloned into the trp- IFN-gamma plasmid so that a new plasmid is generated in which both PDF and IFN-gamma are under the control of the trp promoter.

To determine the effect of the PDF gene on the level of retained formylated IFN-gamma, *E. Coli* K-12 strain W3110G is transformed to produce two transformant strains, one with the plasmid containing PDF and IFN-gamma and one with the plasmid containing only IFN-gamma. High level synthesis of the proteins is achieved by culturing W3110G in the presence of IAA as described. Crude extracts prepared from IAA-induced cultures of the two transformed strains are assayed for PDF activity by the method of Adams (1968) and recombinant IFN-gamma is isolated from both strains and analyzed by RP-HPLC to evaluate f-Met retention. Using this approach, results would be obtained similar to those described for BST in Example 3. Thus, levels of detectable f-Met- IFN-gamma would be advantageously eliminated.

One skilled in the art would appreciate that by using this approach, f-Met retention could be minimized or eliminated in essentially any recombinant protein of interest which normally shows some degree of f-Met retention following microbial production.

The following references may be useful in understanding or practicing the invention. Inclusion of a reference in the following list, however, is not intended to be an admission that any such reference constitutes prior art with respect to the present invention.

REFERENCES

Adams, J. M.: On the release of the formyl group from nascent protein. *J. Mol. Biol.* 33 (1968) 571–589.

Azuma C. Tanabe T., Konishi M., Kinashi T., Noma T., Matsuda F., Yaoita Y., Takatsu K., Hammarstrom L., Smith C. I., et al. Cloning of cDNA for human T-cell replacing factor (interleukin-5) and comparison with the murine homologue. *Nucleic Acids Res* 14(22), (1986) 9149–9158.

Bogosian, G., Violand, B. N., Dorward-King, E. J., Workman, W. E., Jung, P. E. and Kane, J. F.: Biosynthesis and incorporation into protein of norleucine by *Escherichia coli. J. Biol. Chem.* 264 (1989) 531–539.

Bogosian, G., Violand, B. N., Jung, P. E. and Kane, J. F.: Effect of protein overexpression on mistranslation in *Escherichia coli*. In: Hill, W. E., Dahlberg, A., Garrett, R. A., Moore, P. B., Schlessinger, D. and Warner, J. R. (Eds.), The Ribosome: Structure, Function, and Evolution. American Society for Microbiology, Washington, D.C., (1990), 546–558.

Calcott, P. H., Kane, J. F., Krivi, G. G. and Bogosian, G.: Parameters affecting production of bovine somatotropin in *Escherichia coli* fermentations. *Dev. Indust. Microbiol.* 29 (1988) 257–266.

Clogston, C. L., Hsu, Y. R., Boone, T. C. and Lu, H. S.: Detection and quantitation of recombinant granulocyte colony-stimulating factor charge isoforms: comparative analysis by cationic-exchange chromatography, isoelectric focusing gel electrophoresis, and peptide mapping. *Anal. Biochem.* 202 (1992) 375–383.

Coleman, J.: Characterization of the *Escherichia coli* gene for 1-acyl-sn-glycerol-3-phosphate acyltransferase (plsC). *Mol. Gen. Genet.* 232 (1992) 295–303.

Derynck R., Leung D. W., Gray P. W., Goeddel D. V. Human interferon gamma is encoded by a single class of mRNA. *Nucleic Acids Res* 10(12), (1982) 3605–3615.

Dong, M. S., Guo, Z., Philips, D. R., Bell, L. C., Howard, E., Blair, I. A., Gillam, E. M. J., Baba, T., Waterman, M. R. and Guengerich, F. P.: Retention of N-formylmethionine in recombinant bacterial cytochrome P450 enzymes containing the N-terminal sequence MALLLAVFL. *FASEB J.* 9 (1995) A1486.

Eisenstein, E. Cloning, Expression, Purification, and Characterization of Biosynthetic Threonine Deaminase from *Escherichita coli. Journal of Biological Chemistry* 266:9 (1991) 5801–5807.

Guillon, J. M., Mechulam, Y., Schmitter, J. M., Blanquet, S. and Fayat, G.: Disruption of the gene for Met-tRNA-fMet formyltransferase severely impairs growth of *Escherichia coli. J. Bacteriol.* 174 (1992) 4294–4301.

Gutterson, N. I., and Koshland, Jr., D. E. Replacement and amplication of bacterial genes with sequences altered in vitro. *Proc. Nat'l. Acad. Sci. USA* 80 (1983) 4894–4898.

Hamilton, C. M., Aldea, M., Washburn, B. K., Babitzke, P., and Kushner, S. R. New Method for Generating Deletions and Gene Replacements in *Escherichia coli. Journal of Bacteriology,* 171:9 (1989) 4617–4622.

Hauschild-Rogat, P.: N-formylmethionine as a N-terminal group of *E. coli* ribosomal protein. *Mol. Gen. Genet.* 102 (1968) 95–101.

Hirel, P. H., Schmitter, J. M., Dessen, P., Fayat, G. and Blanquet, S.: Extent of N-terminal methionine excision from *Escherichia coli* proteins is governed by the side-chain length of the penultimate amino acid. *Proc. Natl. Acad. Sci. USA* 86 (1989) 8247–8251.

Hogset, A., Blingsmo, O. R., Gautvik, V. T., Saether, O., Jacobsen, P. B., Gordeladzo, J. O., Alestrom, P. and Gautvik, K. M. Expression of Human Parathyroid Hormone In *Escherichia Coli. Biochemical and Biophysical Research Communications* 166:1 (1990) 50–60.

Honda, S., Asano, T., Kajio, T., and Nishimura, O. *Escherichia coli*-Derived Human Interferon-γ with Cys-Tyr-Cys at the N-Terminus is Partially $N^{\alpha}$-Acylated. *Archives of Biochemistry and Biophysics* 269 (1989) 612–622.

Housman, D., Gillespie, D. and Lodish, H. F.: Removal of formyl-methionine residue from nascent bacteriophage f2 protein. *J. Mol. Biol.* (1972) 163–166.

Kane, J. F., Balaban, S. M. and Bogosian, G.: Commercial production of bovine somatotropin in *Escherichia coli*. In: Sikes, C. S. and Wheeler, A. P. (Eds.), Surface Reactive Peptides and Polymers: *Discovery and Commercialization.* American Chemical Society Books, Washington, D.C., (1990) 186–200.

Livingston, D. M. and Leder, P.: Deformylation and protein synthesis. *Biochemistry* 20 (1969) 435–443.

Marasco, W. A., Phan, S. H., Krutzsch, H., Showell, H. J., Feltner, D. E., Nairn, R., Becker, E. L. and Ward, P. A.: Purification and identification of formyl-methionyl-leucyl-phenylalanine as the major peptide neutrophil chemotactic factor produced by *Escherichia coli. J. Biol. Chem.* 259 (1984) 5430–5439.

Mazel, D., Pochet, S. and Marliere, P.: Genetic characterization of polypeptide deformylase, a distinctive enzyme of eubacterial translation. *EMBO J.* 13 (1994) 914–923.

Meinnel, T. and Blanquet, S.: Characterization of the *Thermus thermophilus* locus encoding peptide deformylase and methionyl-tRNA-fMet formyltransferase. *J. Bacteriol.* 176 (1994) 7387–7390.

Meinnel, T. and Blanquet, S.: Enzymatic properties of *Escherichia coli* peptide deformylase. *J. Bacteriol.* 177 (1995) 1883–1887.

Meinnel, T. and Blanquet, S.: Evidence that peptide deformylase and methionyl-tRNA-fMet formyltransferase are encoded within the same operon in *Escherichia coli. J Bacteriol.* 175 (1993) 7737–7740.

Meinnel, T., Mechulam, Y., and Blanquet, S.: Methionine as translation start signal: A review of the enzymes of the pathway in *Escherichia coli. Biochimie* (Paris) 75 (1993) 1061–1075.

Milligan, D. L. and Koshland, Jr., D. E.: The amino terminus of the aspartate chemoreceptor is formylmethionine. *J. Biol. Chem.* 265 (1990) 4455–4460.

Moskovitz, J., Rahman, M. A., Strassman, J., Yancey, S. O., Kushner, S. R., Brot, N., and Weissbach, H. *Escherichia coli* Peptide methionine Sulfoxide Rductase Gene: Regulation of Expression and Role in Protecting Against Oxidative Damage. *Journal of Bacteriology* 177:3, (1995) 502–507.

Nagata S., Tsuchiya M. Asano S., Kaziro Y., Yamazaki T., Yamamoto O., Hirata Y. Kubota N., Oheda M., Nomura H., et al. Molecular cloning and expression of cDNA for human granulocyte colony—stimulating factor. *Nature* 319:6052 (1986) 415–418.

Peredelchuk, M. Y. and Bennett, G. N.: A method for construction of *E. coli* strains with multiple DNA insertions in the chromosome. Gene 187 (1997) 231–38.

Rabbani, S. A., Yasuda T., Bennett H. P. J., Sung, W. L. Zahab, D. M., Tam, C. S. Goltman, D., and Hendy, G. N. Recobminant Human Parathyroid Hormone Synthesized in *Escherichia coli. Journal of Biological Chemistry* 263:3 (1988) 1307–1313.

Rose, K., Regamey, P., Anderegg, R., Wells, T., Proudfoot, A., Human interleukin-5 expressed in *Escherichia coli* has N-terminal modifications. *Biochem J.* 286 (1992) 825–828.

Sandman, K., Grayling, R. A., and Reeve, J. N. Improved N-terminal Processing of Recombinant Proteins Synthesized in *Escherichia coli. Biotechnology* 13 (1995) 504–506.

Seeburg, P. H., Sias, S., Adelman, J., de Boer, H. A., Hayflick, Jr., Jhurani, P., Goeddel, D. V. and Heyneker, H. L.: Efficient bacterial expression of bovine and porcine growth hormones. *DNA* 2 (1983) 37–45.

Specht, B., Oudenampsen-Kruger, E., Ingendoh, A., Hillenkamp, F., Lezius, A. G. and Spener, F.: N-terminal variants of fatty acid-binding protein from bovine heart overexpressed in *Escherichia coli. J. Biotechnol.* 33 (1994) 259–269.

Sugimoto, S., Yamaguchi, K. and Yokoo, Y.: Isolation and characterization of recombinant eel growth hormone expressed in *Escherichia coli. J. Chromatog.* 515 (1990) 483–494.

Sugino, T., Tsunasawa, S., Yutani, K., Ogasahaa, K. and Suzuki, M.: Amino-terminally formylated tryptophan synthase α-subunit produced by the trp operon cloned in a plasmid vector. *J. Biochem.* 87 (1980) 351–354.

Tsunasawa, S., Yutani, K., Ogasahara, K., Taketani, M., Yasuoka, N., Kakudo, M. and Sugino, Y: Accumulation of amino-terminally formylated tryptophan synthase in amplifying conditions. *Agric. Biol. Chem.* 47:6 (1983) 1393–1395.

Vianney, A., Lewin, T., Breyer, Jr., W. F., Lazzaroni, J. C., Portalier, R., and Wesbster, R. E., Membrane Topology and mUtational Analysis of the TolQ Protein of *Escherichia coli* Required for the Uptake of Macromolecules and Cell Envelope Integrity. *Journal of Bacteriology* 176:3 (1994) 822–829.

Wood, D. C., Salsgiver, W. J., Kasser, T. R., Lange, G. W., Rowold, E., Violand, B. N., Johnson, A., Leimgruber, R. M., Parr, G. R., Siegel, N. R., Kimack, N. M., Smith, C. E., Zobel, J. F., Ganguli, S. M., Garbow, J. R., Bild, G. and Krivi, G. G.: Purification and characterization of pituitary bovine somatotropin. *J. Biol. Chem.* 264 (1989) 14741–14747.

What is claimed is:

1. A method for deformylating recombinant protein produced in a bacterial host cell, which method comprises culturing a bacterial host cell expressing:
   a. a first expressible DNA sequence encoding a peptide deformylase enzyme operably linked to a promoter operable in said bacterial host cell; and
   b. a second expressible DNA sequence encoding a recombinant protein operably linked to a promoter operable in said bacterial host cell;
   wherein said bacterial host cell has increased production of peptide deformylase enzyme in an amount effective to increase deformylation of said recombinant protein.

2. The method of claim 1 in which said recombinant protein is *E. coli* tryptophan synthase alpha, tryptophan synthase beta, bovine somatotropin, eel growth hormone, *E. coli* 1-acyl-sn-glycerol-3-phosphate acyltransferase, human granulocyte colony-stimulating factor, bovine fatty acid-binding protein, bovine cytochrome P450, methanothermus fervidus histonea, human interleukin-5, human parathyroid hormone, human gamma-interferon, *E. coli* threonine deaminase, or *E. coli* TolQ membrane protein.

3. The method of claim 2 in which said recombinant protein is human granulocyte colony stimulating factor, bovine somototropin, human gamma interferon or human interleukin-5.

4. A method for deformylating bovine somatotropin produced in a bacterial host cell, which method comprises culturing a bacterial host cell expressing:
   a. a first expressible DNA sequence encoding a peptide deformylase enzyme operably linked to a promoter operable in said bacterial host cell; and
   b. a second expressible DNA sequence encoding bovine somatotropin operably linked to a promoter operable in said bacterial host cell;
   wherein said bacterial host cell has increased production of peptide deformylase enzyme in an amount effective to increase deformylation of said bovine somatotropin.

5. A method for production, in a transformed bacterial host cell, of a recombinant protein having a diminished retention of N-formyl methionine, which method comprises:
   a. Transforming a bacterial host cell with DNA comprising:
      (i) a first expressible DNA sequence encoding a peptide deformylase enzyme operably linked to a promoter operable in said bacterial host cell and
      (ii) a second expressible DNA sequence encoding a recombinant protein operably linked to a promoter operable in said bacterial host cell,
   b. Identifying a transformed bacterial host cell having both of said first and second expressible sequences, and
   c. Culturing said transformed bacterial host cell identified in step b under conditions which cause coexpression of said recombinant protein and said peptide deformylase enzyme.

6. A method for production, in a transformed bacterial host cell, of bovine somatotropin having a diminished retention of N-formyl methionine, which method comprises:
   a. Transforming a bacterial host cell with DNA comprising:
      (i) a first expressible DNA sequence encoding a peptide deformylase enzyme operably linked to a promoter operable in said bacterial host cell and
      (iii) a second expressible DNA sequence encoding bovine somatotropin operably linked to a promoter operable in said bacterial host cell,
   b. Identifying a transformed bacterial host cell having both the first and second expressible sequences, and
   c. Culturing said transformed bacterial host cell identified in step b under conditions which cause coexpression of said bovine somatotropin and said peptide deformylase enzyme.

7. The method of claim 5 in which said recombinant protein is *E. coli* tryptophan synthase alpha, tryptophan synthase beta, bovine somatotropin, eel growth hormone, *E. coli* 1-acyl-sn-glycerol-3-phosphate acyltransferase, human granulocyte colony-stimulating factor, bovine fatty acid-binding protein, bovine cytochrome P450, methanothermus fervidus histonea, human interleukin-5, human parathyroid hormone, human gamma-interferon, *E. coli* threonine deaminase, or *E. coli* TolQ membrane protein.

8. The method of claim 7 in which said recombinant protein is human granulocyte colony stimulating factor, bovine somototropin, human gamma interferon or human interleukin-5.

9. The method of claim 1, 2, 3, 4, 5, 7, or 8 in which the amino acid sequence of said peptide deformylase is substantially the same as the amino acid sequence of the peptide deformylase enzyme endogenous to said bacterial host cell.

10. The method of claim 1, 2, 3, 4, 5, 7, or 8 in which said bacterial host cell is a member of the enterobacteriaceae family.

11. The method of claim 5, 6, 7 or 8 wherein
   (i) said first expressible DNA sequence is on a DNA molecule comprising at least one marker gene,
   (ii) said second expressible DNA sequence is on a DNA molecule comprising at least one marker gene and
   (iii) said transformed bacterial host cell is identified as having a marker trait conferred by at least one of the marker genes.

12. The method of claim 5, 6, 7 or 8 in which said first and second expressible DNA sequences are operably linked to different promoters.

13. The method of claim 12 in which at least one of said promoters is an indole acrylic acid inducible trp promoter.

14. The method of claim 12 in which said first and second expressible DNA sequences are on the same DNA molecule which molecule comprises at least one marker gene.

15. The method of claim 12 in which said first and second expressible DNA sequences are on different DNA molecules each of which comprises at least one marker gene.

16. The method of claim 5, 6, 7 or 8 in which said first and second expressible DNA sequences are operably linked to the same promoter.

17. The method of claim 16 in which said promoter is an indole acrylic acid inducible trp promoter.

18. The method of claim 5, 6, 7 or 8 in which said transformed bacterial host cell produces the protein encoded by said second expressible DNA sequence at a level which is greater than about 80% of the level produced by a bacterial host cell which, otherwise identical, does not contain said first expressible DNA sequence.

19. The method of claim 5, 7, 8, or 6 in which at least one of said expressible DNA sequences is stably integrated into the bacterial chromosome.

20. The method of claim 1, 2, 3, 4, 5, 7, or 8 in which said bacterial host cell is *E. coli*.

21. The method of claim 20 in which the amino acid sequence of said peptide deformylase is substantially the same as the amino acid sequence of *E. coli* peptide deformylase enzyme.

22. The method of claim 20 in which said bacterial host cell is of an *E. coli* K12 strain.

23. A method for increasing the amount of peptide deformylase produced in an *E. coli* host cell which method comprises:

a. Transforming an *E. coli* host cell with a DNA molecule comprising:
   (i) a marker gene and
   (ii) an expressible DNA sequence encoding an *E. coli* peptide deformylase enzyme operably linked to a promoter operable in *E. coli*, b. Identifying a transformed *E. coli* host cell having a marker trait conferred by the marker gene, and c. Culturing said transformed *E. coli* host cell indentified in step b under conditions which cause said transformed *E. coli* host cell to produce more peptide deformylase than an untransformed *E. coli* host cell.

24. The method of claim 23 in which said promoter is chemically inducible and said transformed *E. coli* host cell is cultured in the presence of an amount of inducer compound sufficient to increase peptide deformylase production to a desired level which is between the production level of an untransformed *E. coli* host cell and the maximal production level of said transformed *E. coli* host cell.

25. The method of claim 24 in which said promoter is an indole acrylic acid inducible trp promoter and said inducer compound is indole acrylic acid.

26. A transformed *E. coli* host cell comprising:
a) DNA sequence encoding an *E. coli* peptide deformylase enzyme operably linked to a promoter operable in *E. coli*, which transformed *E. coli* host cell is able to produce more peptide deformylase enzyme than an untransformed *E. coli* host cell, and
b) a DNA sequence encoding a recombinant protein operably linked to a promoter operable in *E. coli*.

27. The transformed *E. coli* host cell of claim 26 in which said recombinant protein is *E. coli* tryptophan synthase alpha, tryptophan synthase beta, bovine somatotropin, eel growth hormone, *E. coli* 1-acyl-sn-glycerol-3-phosphate acyltransferase, human granulocyte colony-stimulating factor, bovine fatty acid-binding protein, bovine cytochrome P450, methanothermus fervidus histonea, human interleukin-5, human parathyroid hormone, human gamma-interferon, *E. coli* threonine deaminase, or *E. coli* TolQ membrane protein.

28. The tranformed *E. coli* of claim 27 in which said recombinant protein is human granulocyte colony-stimulating factor, bovine somototropin, human gamma interferon or human interleukin-5.

29. A transformed *E. coli* host cell which comprises:
a. a first expressible DNA sequence encoding an *E. coli* peptide deformylase enzyme operably linked to a promoter operable in *E. coli*; and
b. a second expressible DNA sequence encoding bovine somatotropin operably linked to a promoter operable in *E. coli*;
wherein said transformed *E. coli* host cell is able to produce bovine somatotropin which contains less formylated methionine than that produced by a transformed *E. coli* host cell which, otherwise identical, is not transformed with said first DNA sequence.

30. The transformed *E. coli* host cell of claim 29 wherein
(i) said first expressible DNA sequence is on a DNA molecule comprising at least one marker gene,
(ii) said second expressible DNA sequence is on a DNA molecule comprising at least one marker gene and
(iii) said transformed *E. coli* host cell has a marker trait conferred by at least one of the marker genes.

31. The transformed *E. coli* host cell of claim 29 in which said peptide deformylase enzyme and said bovine somatotropin are operably linked to the same promoter.

32. A DNA composition which gives a bacterial host cell transformed with said DNA composition the ability to produce recombinant protein having a diminished retention of N-formyl methionine, which DNA composition comprises:
a. a first expressible DNA sequence encoding a peptide deformylase enzyme operably linked to a promoter operable in said bacterial host cell, and
b. a second expressible DNA sequence encoding a recombinant protein operably linked to a promoter operable in said bacterial host cell.

33. A DNA composition which gives a bacterial host cell transformed with said DNA composition the ability to produce bovine somatotropin having a diminished retention of N-formyl methionine, which DNA composition comprises:
a. a first expressible DNA sequence encoding a peptide deformylase enzyme operably linked to a promoter operable in said bacterial host cell, and
b. a second expressible DNA sequence encoding bovine somatotropin operably linked to a promoter operable in said bacterial host cell.

34. The DNA composition of claim 32 or 33 which comprises:
a. a first DNA molecule comprising a first marker gene and said first expressible DNA sequence operably linked to a first promoter, and
b. a second DNA molecule comprising a second marker gene and said second expressible DNA sequence operably linked to a second promoter.

35. The DNA composition of claim 32 or 33 which comprises a DNA molecule comprising:
a. a marker gene,
b. said first expressible DNA sequence operably linked to a first promoter, and
c. said second expressible DNA sequence operably linked to a second promoter.

36. The DNA composition of claim 23 or 33 which comprises a DNA molecule comprising:
a. a marker gene, and
b. said first and second DNA sequences operably linked to a single promoter.

* * * * *